United States Patent [19]

Jaedicke et al.

[11] Patent Number: 5,276,209

[45] Date of Patent: Jan. 4, 1994

[54] PREPARATION OF POLYENES

[75] Inventors: Hagen Jaedicke, Ludwigshafen; Klaus Kaiser, Neustadt; Manfred Hamm, Osthofen, all of Fed. Rep. of Germany

[73] Assignee: BASF Aktiengesellschaft, Ludwigshafen, Fed. Rep. of Germany

[21] Appl. No.: 914,128

[22] Filed: Jul. 17, 1992

[30] Foreign Application Priority Data

Jul. 19, 1991 [DE] Fed. Rep. of Germany ....... 4123994

[51] Int. Cl.$^5$ ............................................. C07C 67/02
[52] U.S. Cl. ................................................... 560/260
[58] Field of Search ........................................ 560/260

[56] References Cited

U.S. PATENT DOCUMENTS 2,165,962  7/1939  Mueller-Cunradi ................ 558/51
4,110,538  8/1978  Décor ................................. 560/11
4,474,983  10/1984 Chabardes et al. ................. 560/260

OTHER PUBLICATIONS

Organic Reactions, vol. 14 pp. 357-368 (1965).
Chem. Abstr. vol. 33. (Oct. 20, 1939) No. 20 8209-8212.
J. Org. Chem. vol. 41, No. 20, 1976, pp. 3287-3293 "Vitamin A ... Sulfone Approach" by Gary Olson et al.
Bull. Soc. Chem., FR, 1985, II pp. 130-131 "Tables des Matières".
Helv. Chim. Acta vol. 59 (1976) pp. 387-396 No. 44 Synthesis of Vitamin A ... Route by Manchand et al.

Primary Examiner—Jose' G. Dees
Assistant Examiner—Joseph M. Conrad
Attorney, Agent, or Firm—Keil & Weinkauf

[57] ABSTRACT

An improved process for the preparation of polyenes by the Julia reaction comprises carrying out the allylation of the anion of an allyl aryl sulfone generated a strong base, and the elimination of arylsulfinic acid to form a double bond in the same inert polar solvent which is immiscible with water, preferably in a ketone of the formula I $$R^1-CO-R^2 \qquad (I)$$

where $R^1$ and $R^2$ are each straight-chain or branched alkyl of 2 to 4 carbons, or $R^1$ and $R^2$ together are tetramethylene or pentamethylene. The process is particularly important for the preparation of vitamin A derivatives. In the preparation of vitamin A aldehyde, for example, it is advantageous to use the same alkali metal alcoholate as strong base in both stages so that the conversion can be carried out as one-pot reaction.

8 Claims, No Drawings

PREPARATION OF POLYENES

The invention relates to an improved process for the preparation of polyenes by reacting α-allylic aryl sulfones with α-allylic halides or other allylating agents and subsequent elimination of arylsulfinates.

By polyenes are meant very generally unsaturated aliphatic hydrocarbons with at least three conjugated double bonds in the molecule, i.e. compounds with a plurality of alternating single and double bonds. Examples of naturally occurring colored polyenes are lycopene and β-carotene. Some of the naturally occurring compounds are of interest as food colorings, while others have achieved importance as medicinal agents. The most important polyenes are the carotenoids, retinoids and, specifically, vitamin A.

Consistent with their importance, a wide variety of methods has been developed for preparing this class of substance (for review, cf. O. Isler Carotenoids, Birkhäuser-Verlag, 1971).

Particularly well known methods for preparing polyenes are the Wittig reaction, i.e. the linkage of α,β-unsaturated aldehydes with phosphonium ylides (cf., for example, "Organic Reactions", vol. 14, published by John Wiley, New York, 1965); the Müller-Cunradi reaction, i.e. the addition of enol ethers onto dialkyl acetals of α,β-unsaturated aldehydes (cf., for example, U.S. Pat. No. 2,165,962 and Chem. Abstr. 33 (1939) 8210) and the Julia method, i.e. the alkylation of α-metalated sulfones with allyl halides and subsequent elimination of a sulfinate (cf. M. Julia and D. Arnould, Bull. Soc. Chim. Fr. (1973) 743 and 746). This method has been used, for example, by G. L. Olsen et al. in J. Org. Chem. 41 (1976) 3287 to synthesize all-trans vitamin A in the following way, cially the elimination of the sulfinate, requires another reaction medium.

For example, the preparation of vitamin A or its derivatives by the method described in J. Org. Chem. 41 makes use of a system composed of $NaNH_2$, liquid ammonia and tert-butanol or of tetrahydrofuran (THF) and lithium diisopropylamide. In both cases, once the reaction is complete the mixture is poured into water and extracted with diethyl ether.

It is an object of the present invention to improve the process for the preparation of polyenes by reaction of α-metallated sulfones with alkylating agents such as, in particular, allyl halides to eliminate the serious disadvantages of the prior art and to allow it to be carried out advantageously on the industrial scale.

We have found that this object is achieved by carrying out all the steps necessary in this process, such as the allylation, any washing of the reaction mixture with water, elimination of the sulfinate, any subsequent further washing with water which is necessary, and even further reaction of the resulting olefin, in the same solvent when the solvent is an inert polar solvent which is immiscible with water and is a ketone or ether. It was surprising that in this advantageous way of carrying out the process the eliminated sodium benzenesulfinate results substantially in the form of a solid and can therefore be recycled in a particularly straight-forward manner.

The present invention accordingly relates to a process for the preparation of polyenes by the Julia reaction, i.e. the allylation of an anion of an allyl aryl sulfone with an allyl compound in the α-position and subsequent elimination of the arylsulfinic acid using a strong base to form an olefinic double bond, which comprises carrying out the allylation of the allyl aryl sulfone and the elimination of the arylsulfinic acid in the same inert,

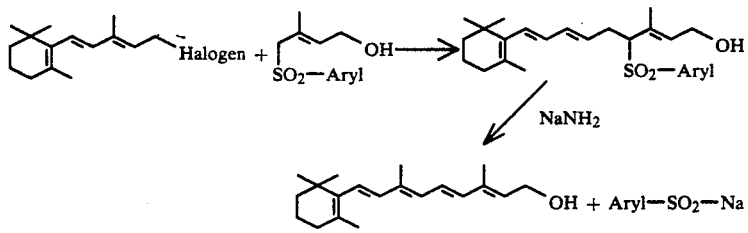

Furthermore, DE-A 27 08 210 describes a process for the preparation of sulfone acetals in the sulfones are metallated and allylated in a basic polar aprotic medium which is miscible with water, such as dimethylformamide or dimethyl sulfoxide. The resulting mixture is subsequently hydrolyzed and the required product is extracted into a solvent which is immiscible with water, for example diisopropyl ether.

All the processes hitherto described for the preparation of polyenes by alkylation of sulfones have serious disadvantages concerning the solvent used. Thus, the alkylation reaction mixture is normally poured into ice-water, and the required product must be isolated from the aqueous phase. This results in most of the solvent used for the reaction being lost and therefore leads to heavy pollution of the effluent. In addition, a solvent which is immiscible with water is required for the extraction of the required product out of the aqueous phase. The subsequent reaction of the sulfone, espepolar solvent which is immiscible with water, preferably in a ketone of the formula I $$R^1-CO-R^2 \qquad (I)$$

where $R^1$ and $R^2$ are each straight-chain or branched alkyl of 2 to 4 carbon atoms, or $R^1$ and $R^2$ together are tetramethylene or pentamethylene.

The process according to the invention can be carried out particularly advantageously by carrying out the allylation of the allyl aryl sulfone and the elimination of the arylsulfinic acid in diethyl ketone, dipropyl ketone, cyclopentanone, cyclohexanone or diisopropyl ether, preferably indiethyl ketone.

The present invention particularly relates to a process for the preparation of vitamin A derivatives by allylation of an anion of an allyl aryl sulfone of the formula II

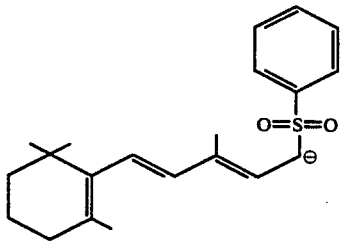

with an allyl compound of the formula III

where X is a negative leaving group and where $R^3$ is H, —$CH_2$—$OCOCH_3$, —$COOR^4$ or

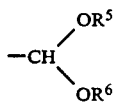

where $R^4$, $R^5$ and $R^6$ are each alkyl of 1 to 4 carbons, or $R^5$ and $R^6$ together are ethylene or propylene which can be substituted by one or more methyl groups, to give an aryl sulfone of the formula IV

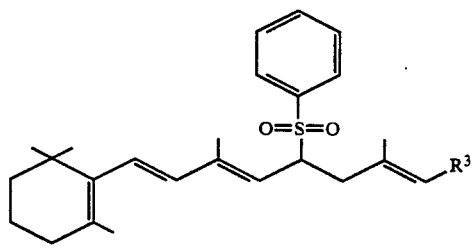

and subsequent elimination of the arylsulfinic acid to form the corresponding vitamin A derivative, which comprises carrying out the allylation of the allyl aryl sulfone and the elimination of the arylsulfinic acid in a ketone of the formula I $R^1$—CO—$R^2$ (I)

where $R^1$ and $R^2$ are each straight-chain or branched alkyl of 2 to 4 carbons, or $R^1$ and $R^2$ together are tetramethylene or pentamethylene.

The process for the preparation of vitamin A derivatives, especially of vitamin A acetate, is also particularly advantageous when the alkylation of the ally aryl sulfone and the elimination of the arylsulfinic acid are carried out in diethyl ketone.

By polyenes are meant in general unsaturated aliphatic compounds which contain at least three conjugated double bonds in the molecule. The improvements according to the invention can be applied to the preparation of all polyenes which can in principle be obtained by the Julia method. Examples of polyenes which can be prepared by the process according to the invention are: β-carotene, astaxanthin, canthaxanthin, neurosporaxanthin, and vitamin A derivatives such as vitamin A alcohol (retinol), vitamin A acetate, vitamin A acid and vitamin A aldehyde (retinal). The process is particularly advantageous for the preparation of vitamin A derivatives, especially vitamin A acetate and vitamin A aldehyde.

The allyl aryl sulfones used as starting materials are obtained in a conventional manner known by reacting allyl alcohols or allyl halides with salts of arylsulfinic acids (cf., for example, D. Arnould et al. in Bull. Soc. Chim. France (1985) II, 130, and P. S. Manchand et al. in Helv. Chim. Acta 59 (1976) 387).

Examples of suitable allyl aryl sulfones are: β-ionylidenyl phenyl sulfone of the formula II, retinyl phenyl sulfone or 3-(5,5-dimethyl-1,3-dioxan-2-yl)crotyl phenyl sulfone.

Suitable allyl compounds of the formula III

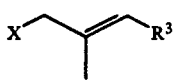

are all compounds of this formula where X is a negative leaving group and $R^3$ has the abovementioned meanings.

Negative leaving groups are radicals which can be converted by a base into an anion. Examples of such groups are, in particular, halogen such as, in particular, chloride and bromide; acyloxy such as acetoxy, trifluoroacetoxy and nonafluorobutoxy; sulfonyloxy such as p-toluenesulfonyloxy and methanesulfonyloxy.

Compounds of the formula III where X is Cl or Br are used particularly advantageously. Particular mention may be made of γ-chloroprenal neopentyl glycol acetal, γ-bromoprenal neopentyl glycol acetal, 3-(5,5-dimethyl-1,3-dioxan-2-yl)crotyl chloride, 3-chloromethylcrotonaldehyde neopentyl glycol acetal and vitamin A acetate.

The anions of the allyl aryl sulfones are generated by reaction with a strong base in a solvent. Examples of suitable strong bases are KOH, $KOCH_3$, $NaOCH_3$, $NaNH_2$, KO-tert-butyl.

Care must be taken in this connection that the base does not decompose one of the reactants. For example, $KOCH_3$ must not be used in the allylation with γ-bromoprenyl acetate because it would hydrolyze off the acetyl group, and the resulting prenol would undergo ring closure and not be available for the required reaction. On the other hand, this reaction would succeed with KO-tert-butyl or $NaNH_2$. Simple preliminary tests can be carried out to establish which base can be used.

Alkali metal alcoholates such as $KOCH_3$ and $KOC_2H_5$, especially potassium tert-butylate, are particularly suitable.

The elimination of the arylsulfinic acid also takes place with strong bases Examples of suitable strong bases are NaOH, KOH, $KOCH_3$, $KOC_2H_5$ or KO-tert-butyl.

It is particularly advantageous to use alkali metal alcoholates, especially, when possible, the same as used to generate the anions of the allyl aryl sulfones.

Thus, for example in the preparation according to the invention of vitamin A acetate from β-ionylidenyl phenyl sulfone and γ-bromoprenal acetate, potassium tert-butanolate or $NaNH_2$ is used in the generation of the anion of β-ionylidenyl phenyl sulfone, whereas alkali methylates or alkali metal hydroxides are used in the subsequent elimination of the arylsulfinic acid. Nevertheless, the two stages can be carried out as a one-pot reaction.

The process according to the invention is particularly advantageous for the preparation of retinal, because it is possible in this case very advantageously to employ KOCH₃ or NaOCH₃, preferably KOCH₃, as base in both stages.

Both reaction steps are carried out according to the invention in the same inert solvent which is immiscible with water. Examples of suitable solvents are ketones, such as 4-heptanone (dipropyl ketone), 3-pentanone (diethyl ketone), cyclopentanone and cyclohexanone, and ethers such as diisopropyl ether.

Diethyl ketone is used particularly advantageously. On the other hand, methyl ketones are unsuitable.

The general procedure for carrying out the process according to the invention is to add the suitable strong base to a solution of the allyl phenyl sulfone and of the allylating agent.

The process according to the invention can be used, for example, to prepare polyenes suitable as dyes or active substances very advantageously even on the industrial scale.

EXAMPLE 1

A. Preparation of a solution of a C₁₅ sulfone in diethyl ketone

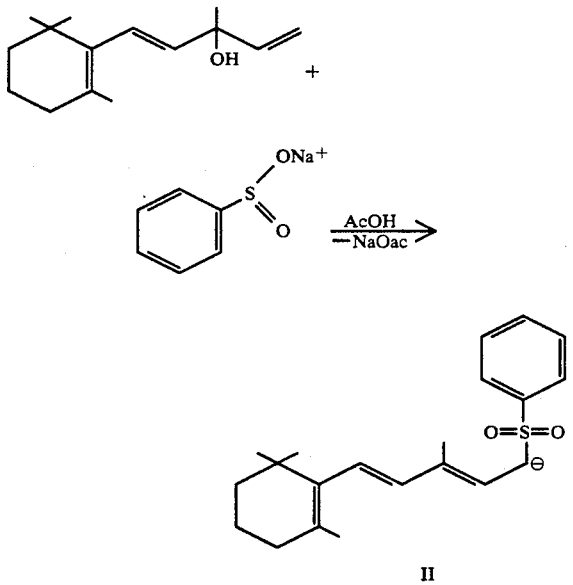

164 g (about 1 mol) of sodium benzenesulfinate were heated in a mixture of 300 ml of water and 350 ml of AcOH to 60° C. At this temperature, 200 g (92–93% pure, corresponding to about 0.87 mol) of vinylionol were added dropwise over the course of 40 minutes (min), and the reaction mixture was then stirred at 60° C. for 4 hours (h). Subsequently 350 ml of diethyl ketone (DEK) were added and, after mixing for 10 min, the phases were separated. The combined organic phases were mixed with 350 ml of water which had been adjusted to pH 8 with concentrated aqueous NaOH. The resulting C₁₅ sulfone in DEK was separated off, dried over MgSO₄ and filtered.

B. Allylation, benzenesulfinate elimination and hydrolysis in diethyl ketone

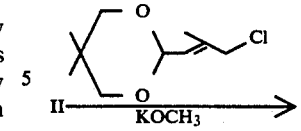

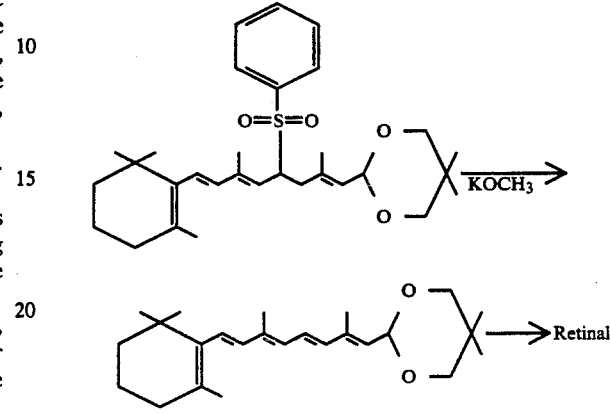

190 g of pure γ-neopentyl glycol acetal (prepared as described in DE-A 2 917 413) were added to the C₁₅ sulfone solution in DEK prepared as in Example 1A, and then, while cooling at 0° C., a suspension of 150 g (about 2.1 mol) of potassium methylate in 350 ml of DEK was added over the course of 1 h. The reaction mixture was stirred at room temperature (RT) for 1 h and then heated to 60° C. and, after stirring for a further 60 min, the precipitated mixture of KCl and potassium benzenesulfinate was dissolved in 250 ml of water, and the lower aqueous phase was separated off.

The organic phase was mixed with 300 ml of isopropanol and 300 ml of a 2% strength H₂SO₄, and stirred at 40° C. for 10 min. After cooling to 20° C., the aqueous phase was separated off, and the organic phase was concentrated under reduced pressure. 222 g (corresponding to a yield of 84% of theory) of pure retinal, which was composed of 79% of the all-trans form, 18% of the 13-cis isomer and about 1% of the 9-cis isomer, were obtained.

EXAMPLE 2

Allylation, benzenesulfinate elimination and hydrolysis in 4-heptanone (dipropyl ketone, DPK)

34.5 g of pure C₁₅ sulfone (prepared as in Example 1A) were dissolved in 100 ml of DPK, and 23 g of γ-chloroprenal neopentyl glycol acetal were added. Subsequently, while cooling at about 20° C., 18 g of potassium methylate powder were introduced a little at a time over the course of 30 min. The mixture was stirred at RT for 20 min and then heated to 55° C. and stirred at 55° C. for 2 h. Subsequently 50 ml of water were added dropwise and, after mixing, the lower phase was separated off. The upper phase was mixed with 30 ml of isopropanol and 30 ml of 2% strength H₂SO₄ and heated at 70° C. for 30 min, and then the phases were separated. 24.1 g of retinal predominantly in the all-trans form were isolated from the organic phase.

EXAMPLE 3

The process was carried out as described in Example 2 but 100 ml of cyclohexanone were used in place of 100 ml of dipropyl ketone. After hydrolysis and concentration of the organic phase, 28.4 g of 82% pure retinal were obtained.

EXAMPLE 4

Recycling of potassium benzenesulfinate

The aqueous solution of KCl and potassium benzenesulfinate obtained as in Example 1B was mixed with 300 ml of glacial acetic acid, the mixture was heated to 60° C. and then 178 g (0.81 mol) of vinylionol were added dropwise over the course of 25 min, and the mixture was then stirred at 60° C. for 1 h. It was then extracted 3× with 100 ml of DEK, and the combined extracts were washed with dilute sodium carbonate solution until acidfree. HPLC showed a yield of 92% cis-trans-$C_{15}$ sulfone based on vinylionol.

EXAMPLE 5

Allylation of 3-(5,5-dimethyl-1,3-dioxan-2-yl-)crotyl phenyl sulfone (1) with 3-(5,5-dimethyl-1,3-dioxan-2-yl)-crotyl chloride (2)

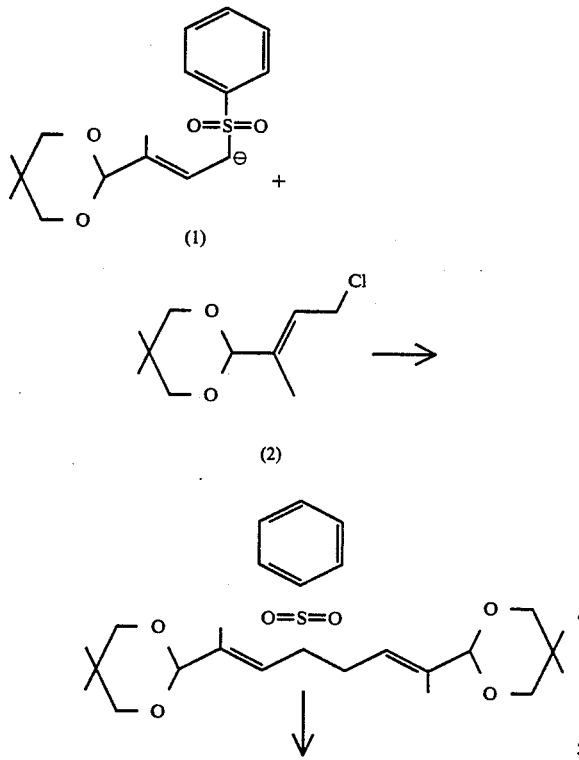

2,7-dimethyloctatrienediol

A. Preparation of the phenyl sulfone 1

42 g (0.25 mol) of sodium benzenesulfinate were added to a solution of 52.6 g (0.25 mol) of 3-(5,5-dimethyl-1,3-dioxan-2-yl)crotyl chloride (prepared as described in Liebigs An. Chem. (1976) 2194) in 200 ml of DEK, the resulting mixture was refluxed for 4 h, the NaCl which had crystallized was filtered off, and the precipitate was washed with 300 ml of DEK.

B. Allylation, benzenesulfinate elimination and hydrolysis 52.6 g (0.25 mol) of 3-(5,5-dimethyl-1,3-dioxan-2-yl)crotyl chloride (2) were added to the solution of the phenyl sulfone 1 obtained as in Example 5A, and the mixture was cooled to 0° C. Subsequently 16.4 g of powdered KOH were added and the mixture was then stirred at 0° C. for 60 min. Then 21 g (0.3 mol) of powdered potassium methylate were added, and the mixture was allowed to warm to RT while stirring. After 2 h, all the allylation product had been converted into 2,7-dimethyloctatrienedial di(neopentyl glycol acetal) After the reaction mixture had been washed with water, 68 g (corresponding to 81% of theory) of 2,7-dimethyloctatrienedial di(neopentyl glycol acetal) (3) were obtained, mainly in the trans form. The diacetal (3) was completely hydrolyzed with DEK and 200 ml of dilute $H_2SO$ in a 2-phase system to 2,7-dimethyloctatrienedial. The target product was isolated in a yield of 79% based on 3-(5,5-dimethyl-1,3,-dioxan-2-yl)crotyl chloride.

EXAMPLE 6

Allylation of 3-(5,5-dimethyl-1,3-dioxan-2-yl-)crotyl phenyl sulfone with 3-chloromethylcrotonaldehyde neopentyl glycol acetal.

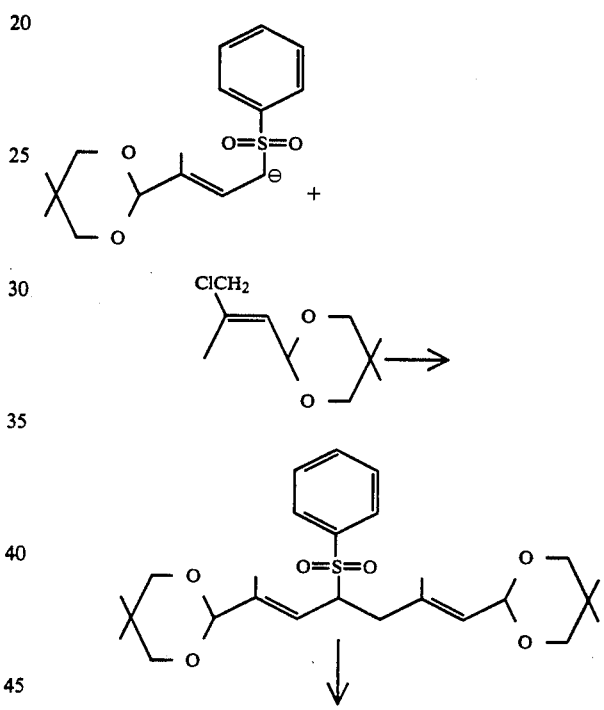

2,6-dimethyloctatrienediol 20.5 g (0.1 mol) of 3-chloromethylcrotonaldehyde neopentyl glycol acetal were added to a solution of 31.0 g (0.1 mol) of 3-(5,5-dimethyl-1,3-dioxan-2-yl)-crotyl phenyl sulfone in 200 ml of DEK prepared as in Example 5A. The mixture was then cooled to 0° C. while stirring, and 17 g (0.24 mol) of solid potassium methylate were added over the course of 20 min. After 1 h the reaction mixture was allowed to warm to RT and was then stirred for 2 h. HPLC checks showed that 30.6 g (corresponding to 91% of theory) of 2,7-bis(5,5-dimethyl-1,3-dioxan-2-yl)-6-methyl-2,4,6-heptatriene had been produced. The reaction mixture was washed with a little water, and 60 ml of isopropanol and 60 ml of 2% strength $H_2SO_4$ and 17.4 g of propionaldehyde were added to the isolated DEK solution of the product for transacetalization. Hydrolysis was complete after stirring at 40° C. for 2 h. The aqueous phase was then separated off, and the organic phase was concentrated. After addition of 50 ml of isopropanol to the residue, 11.1 g (corresponding to 75% of theory) of 2,6-dimethyloctatrienedial crystallized, melting point 99°–100° C.

EXAMPLE 7

Allylation of the $C_{15}$ sulfone from Example 1A with γ-bromoprenyl acetate

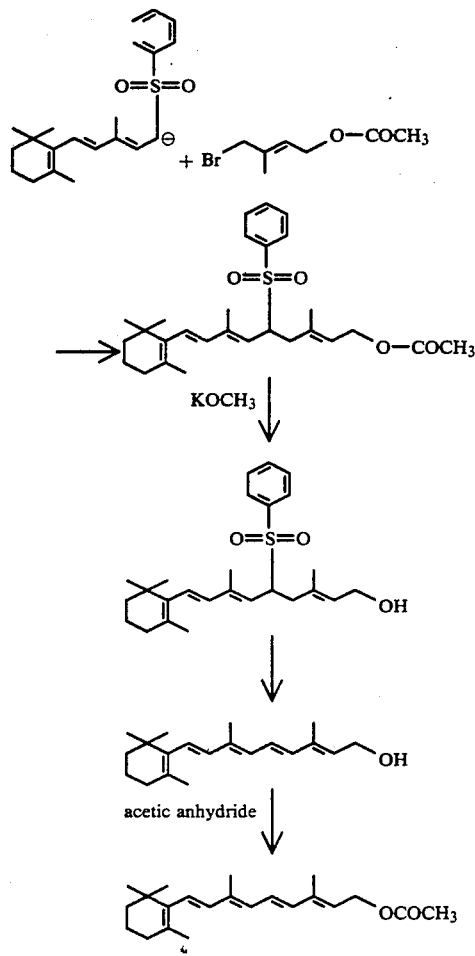

22 g of γ-bromoprenyl acetate (prepared as in Example 1 of U.S. Pat. No. 4,175,204) were added to 34.5 g (0.1 mol) of a $C_{15}$ sulfone in 200 ml of DEK prepared as in Example 1A. The mixture was then cooled to 0° C. and, at this temperature, a solution of 15 g (about 0.13 mol) of potassium tert-butanolate in 100 ml of DEK was added dropwise over the course of 30 min. After a further 60 min, 17 g (0.24 mol) of potassium methylate were added, and the mixture was heated to 70° C. After stirring for 4 hours, 200 ml of water were added and the lower phase was separated off. 30.6 g (0.3 mol) of acetic anhydride and 3 drops of conc. $H_2SO_4$ were added to the upper phase. After 60 min, all the vitamin A alcohol had been esterified. The mixture was washed with dilute sodium carbonate solution until free of acid. The DEK phase contained 26.9 g (82% of theory) of vitamin A acetate, mainly in the trans form. The product was isolated by removing the solvent by evaporation under mild conditions and by crystallization from methanol.

EXAMPLE 8

Alkylation of β-ionylideneethyl phenyl sulfone with γ-chloroprenal neopentyl glycol acetal 34.5 g of β-ionylideneethyl phenyl sulfone ($C_{15}$-sulfone; prepared as described by D. Arnould et al. in Bull. Soc. Chim. France (1985) II, 130) and 22 g of γ-chloroprenal neopentyl glycol acetal were dissolved in 300 ml of diisopropyl ether and the solution was cooled to 0° C. and, at this temperature, 21 g of powdered potassium methylate were added in portions over 1 h. The reaction mixture was then stirred at RT for 1 h and subsequently heated to 60° C. After 1 h the elimination of benzenesulfinate was complete. The potassium benzenesulfinate and KCl byproducts were completely removed from the organic phase with 50 ml of water. The aqueous phase could be used without difficulty for new preparation of $C_{15}$-sulfone from vinylionol. The organic phase with the alkylation/elimination product was mixed with 30 ml of isopropanol, 30 ml of 2% sulfuric acid and 6 g of propanol. The acetal was completely hydrolyzed after 20 min at 60° C. The aqueous phase was separated off, and the organic phase was washed twice with dilute $NaHCO_3$ solution and with water. After drying over $Na_2SO_4$, 279 g of a solution of 25.3 g of retinal in diisopropyl ether were obtained, corresponding to a yield of 89% of theory.

We claim:

1. An improved process for the preparation of polyenes by the Julia reaction, which is the allylation of an anion of an allyl aryl sulfone with an allyl compound in the α-position and subsequent elimination of the arylsulfinic acid using a strong base to form an olefinic double bond, which comprises carrying out the allylation of the allyl aryl sulfone and the elimination of the arylsulfinic acid in the same ketone of the formula I $$R^1-CO-R^2 \qquad (I)$$

where $R^1$ and $R^2$ are each straight-chain or branched alkyl of 2 to 4 carbons, or $R^1$ and $R^2$ together are tetramethylene or pentamethylene.

2. A process as defined in claim 1, wherein the allylation of the allyl aryl sulfone and the elimination of the arylsulfinic acid are carried out in diethyl ketone, dipropyl ketone, cyclopentanone or cyclohexanone.

3. A process as defined in claim 1, wherein the allylation of the allyl aryl sulfone and the elimination of the arylsulfinic acid are carried out in diethyl ketone.

4. A process as defined in claim 1 for the preparation of a vitamin A derivative by allylation of an anion of an allyl aryl sulfone of the formula II

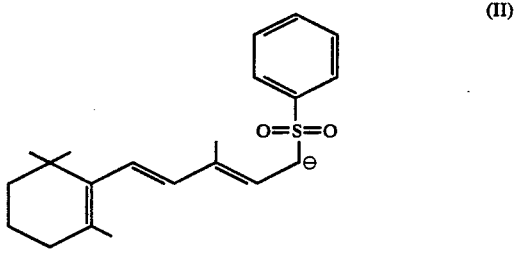

with an allyl compound of the formula III

where X is a negative leaving group and where R³ is H, —CH₂—OCOCH₃, —COOR⁴ or

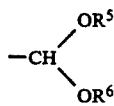

where R⁴, R⁵ and R⁶ are each alkyl of 1 to 4 carbons, or R⁵ and R⁶ together are ethylene or propylene which can be substituted by one or more methyl groups, to give an aryl sulfone of the formula IV

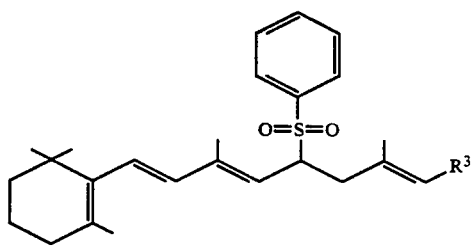 (IV)

and subsequent elimination of the arylsulfinic acid to form the corresponding vitamin A derivative, which comprises carrying out the allylation of the allyl aryl sulfone and the elimination of the arylsulfinic acid in a ketone of the formula I

R¹—CO—R²        (I)

where R¹ and R² are each straight-chain or branched alkyl of 2 to 4 carbon atoms, or R¹ and R² together are tetramethylene or pentamethylene.

5. A process as defined in claim 4, wherein the allylation of the allyl aryl sulfone and the elimination of the arylsulfinic acid are carried out in diethyl ketone.

6. A process as defined in claim 4, wherein the allylation of the allyl aryl sulfone is carried out with an allyl compound of the formula III

 (III)

where X is Cl or Br and R³ is —CH₂—OCOCH₃ or

7. A process as defined in claim 4 for the preparation of a retinal acetal by allylation of an anion of an allyl aryl sulfone of the formula II

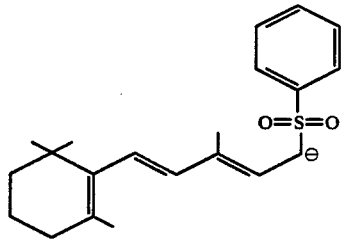 (II)

with an allyl compound of the formula III

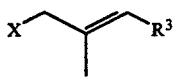 (III)

where X is Cl or Br and R³ is

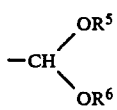

where R⁵ and R⁶ have the meaning stated in claim 5, to give an allyl aryl sulfone of the formula IV

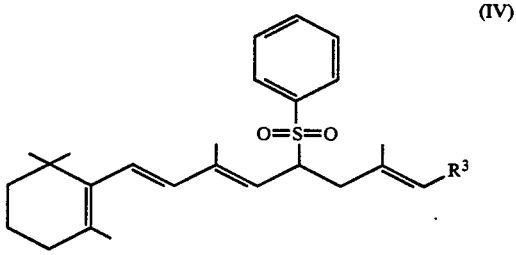 (IV)

and subsequent elimination of the arylsulfinic acid to form the corresponding retinal acetal, which comprises carrying out the allylation of the allyl aryl sulfone and the elimination of the arylsulfinic acid with potassium methylate in diethyl ketone.

8. The process as defined in claim 4 for the preparation of vitamin A acetate by allylation of an anion of an allyl aryl sulfone of the formula II

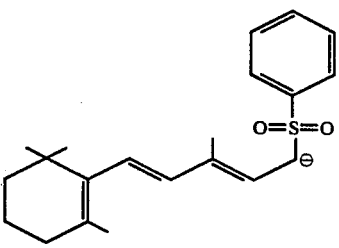 (II)

with an allyl compound of the formula III

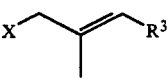 (III)

where X is Cl or Br and R³ is —CH₂—OCOCH₃, to give an allyl aryl sulfone of the formula IV

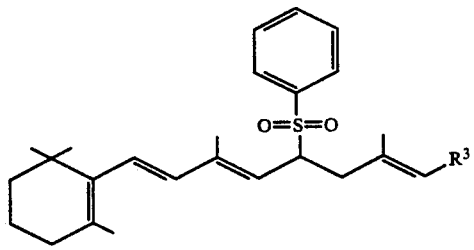

and subsequent elimination of the arylsulfinic acid to form vitamin A acetate, which comprises carrying out the allylation of the allyl aryl sulfone and the elimination of the arylsulfinic acid in diethyl ketone, the strong bases used being potassium tert-butylate for the allylation and alkali metal hydroxides or alkaline metal methylates for the elimination of the arylsulfinic acid.

* * * * *